US012806024B2

(12) United States Patent
Caiazza

(10) Patent No.: US 12,806,024 B2
(45) Date of Patent: Nov. 24, 2026

(54) MOLD FOR OBTAINING A SPACER DEVICE OR A PART THEREOF

(71) Applicant: Tecres S.p.A., Sommacampagna (IT)

(72) Inventor: Emanuele Caiazza, Rome (IT)

(*) Notice: Subject to any disclaimer, the term of this patent is extended or adjusted under 35 U.S.C. 154(b) by 518 days.

(21) Appl. No.: 18/555,067

(22) PCT Filed: Apr. 16, 2022

(86) PCT No.: PCT/IB2022/053585
§ 371 (c)(1),
(2) Date: Oct. 12, 2023

(87) PCT Pub. No.: WO2022/224116
PCT Pub. Date: Oct. 27, 2022

(65) Prior Publication Data

US 2024/0197481 A1 Jun. 20, 2024

(30) Foreign Application Priority Data

Apr. 19, 2021 (IT) ........................ 102021000009905

(51) Int. Cl.
*B32B 41/00* (2006.01)
*A61F 2/30* (2006.01)

(52) U.S. Cl.
CPC ..................... *A61F 2/30942* (2013.01); *A61F 2002/30957* (2013.01)

(58) Field of Classification Search
CPC ........ A61F 2/30942; A61F 2002/30957; A61F 2/28; A61F 2/32; A61F 2/36; A61F 2/38; A61F 2/3859; A61F 2/389; A61F 2/40; A61F 2/3094; A61F 2310/00353; A61F 2002/30556
USPC ............ 156/60, 64, 500, 505, 510, 511, 514
See application file for complete search history.

(56) References Cited

U.S. PATENT DOCUMENTS

2009/0157189 A1 6/2009 Hartman
2013/0295213 A1 11/2013 Lomicka
2018/0319057 A1* 11/2018 Foroni .................... B29C 39/26
2019/0134858 A1 5/2019 Cappelletti

FOREIGN PATENT DOCUMENTS

EP 2526900 A1 † 11/2012
WO 2017134614 † 8/2017

OTHER PUBLICATIONS

COPAL® Knee Moulds—Instructions for Use, Heraeus Medical GmbH, Rev. Jul. 2015 (Jul. 16, 2015).†

* cited by examiner
† cited by third party

*Primary Examiner* — Michael N Orlando
*Assistant Examiner* — Joshel Rivera
(74) *Attorney, Agent, or Firm* — Themis Law

(57) ABSTRACT

A mold for obtaining a spacer device for replacing a joint prosthesis, or a part thereof, includes a first half-shell and a second half-shell.

20 Claims, 5 Drawing Sheets

FIG.3
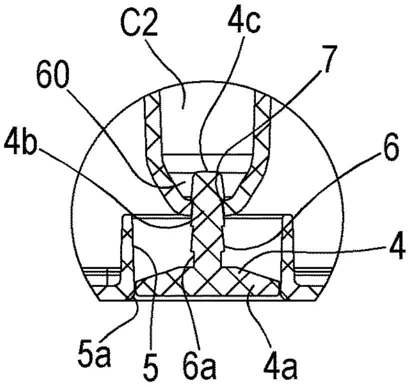
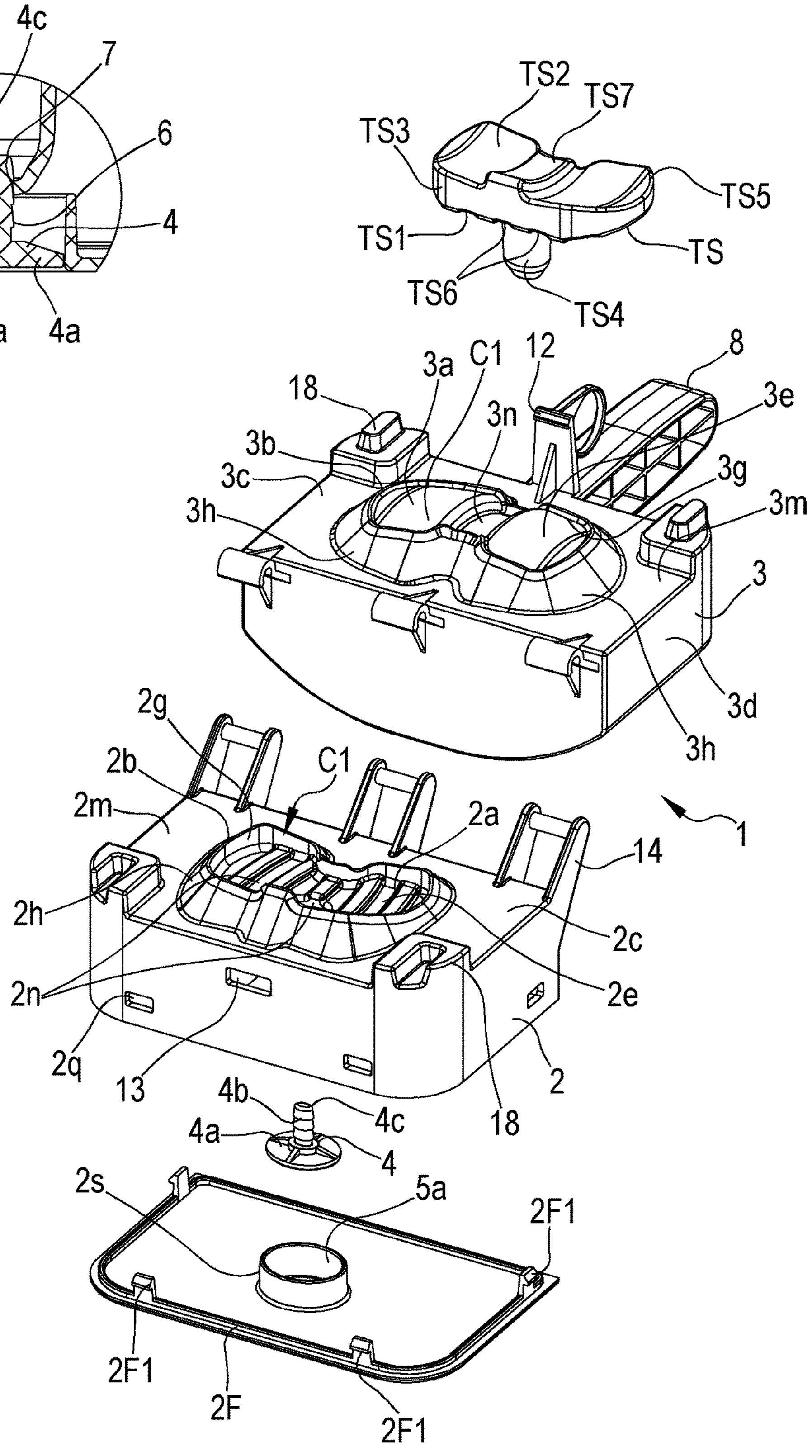
FIG.4

FIG.7
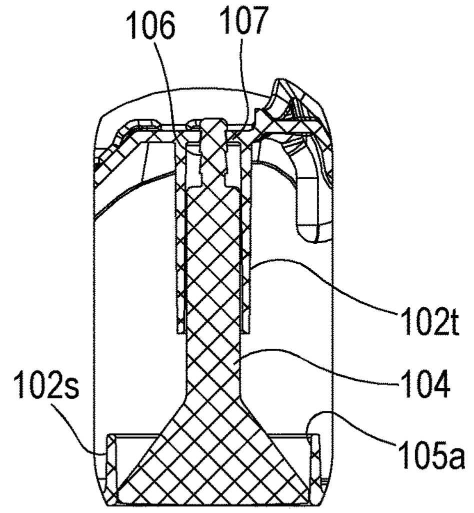
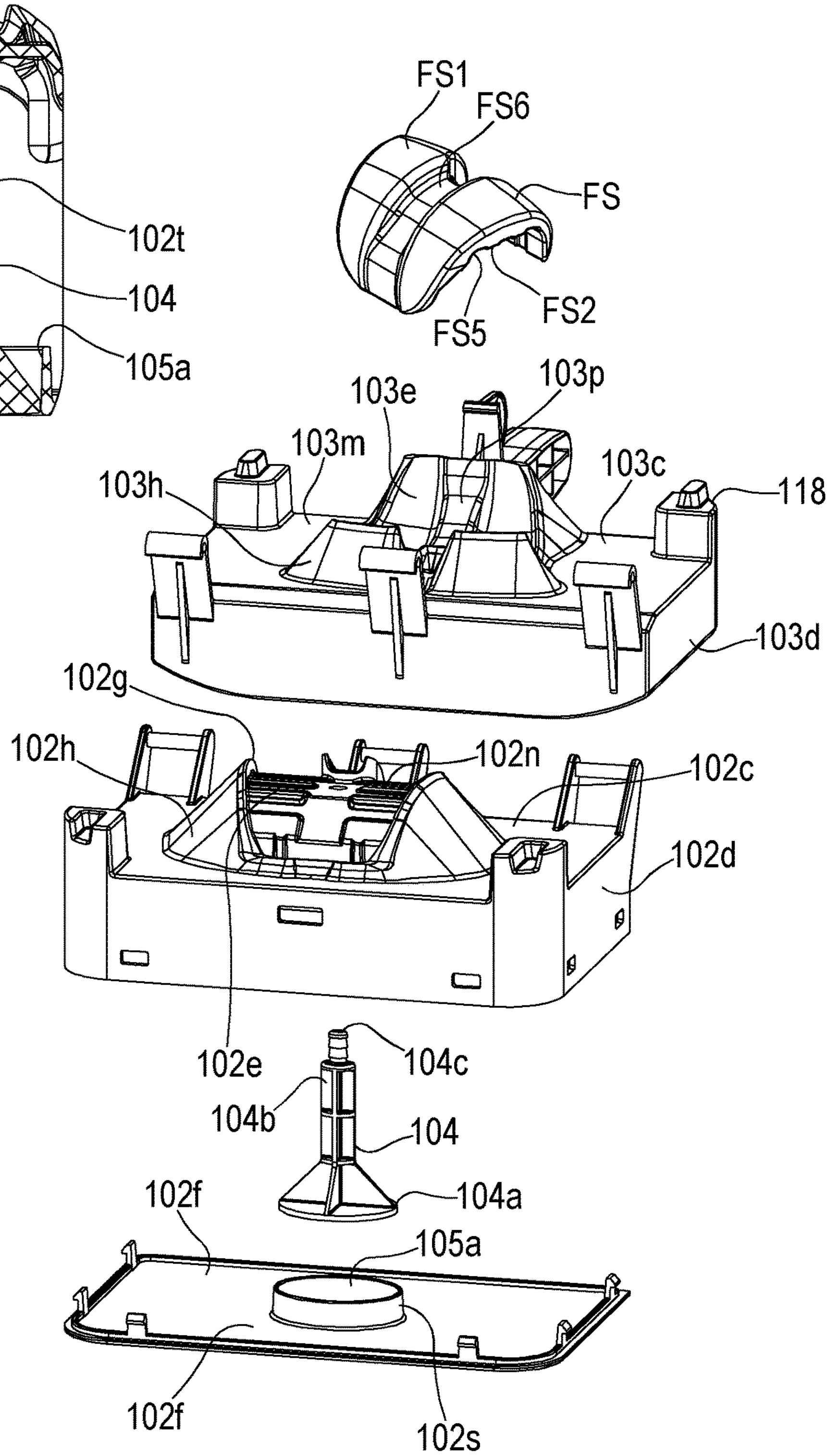
FIG.8

MOLD FOR OBTAINING A SPACER DEVICE OR A PART THEREOF

TECHNICAL FIELD OF THE INVENTION

The present invention relates to a mold for obtaining a spacer device, or part thereof, as well as a method for using such a mold and extracting an element molded therein.

STATE OF THE PRIOR ART

Molds have been proposed for the realisation of joint spacer devices, which are usually made of elastically deformable material, such as silicone or other suitable elastomer material, and intended to be filled with bone cement added with antibiotic or other therapeutic substance, when this is in the phase of fluid and malleable mass, in order to obtain a finished spacer device.

After being hardened in such a mold, the bone cement added with an antibiotic or other therapeutic substance is subsequently removed from it and the resulting joint spacer, once finished, is implanted in the joint space of a patient to treat an ongoing disease in the tissues surrounding that joint space.

Traditional molds have numerous drawbacks.

First, at the end of the molding process, the spacer device may remain attached to the mold material, making it difficult to extract the spacer device quickly and easily.

Moreover, although in most cases these molds are meant to be recycled/disposed of after only one use, they are sometimes reused after a suitable washing process in order to reduce the costs of obtaining spacer devices of the same shape.

It may be the case, however, that such washing does not completely remove traces of antibiotic or therapeutic substances added to the bone cement used for a previous spacer device. This may result in allergic reactions to spacer devices made with an antibiotic to which a patient is not allergic but which have been made in a mold previously used with bone cement containing an antibiotic to which the patient is allergic.

Moreover, the polymerisation of the cement used for the realisation of spacer devices involves an exothermic reaction that brings the cement and the mold material beyond 100° C., while the steam sterilisation (a typical hospital system) used in the possible reuse of the molds brings the molds themselves to about 121° C.

As will be understood from the ensuing disclosure, the succession of heating measures at such high temperatures deforms the live areas of the molds, preventing the repeated formation of perfect spacers or compliance with the necessary requirements.

US2019134858A1 discloses a prior art solution.

OBJECTS OF THE INVENTION

An object of the present invention is to provide a new mold for obtaining a spacer device or a part thereof.

Another object of the present invention is to provide a mold as indicated above capable of ensuring easy and fast extraction of a spacer device molded therein.

Yet another object of the present invention is to provide a mold as indicated above that contains elements such as to ensure that it is used only once.

In accordance with one aspect of the invention, a mold is provided according to claim 1.

Dependent claims refer to preferred and advantageous examples of embodiments of the invention.

BRIEF DESCRIPTION OF THE DRAWINGS

Other features and advantages of the invention will become more evident from the disclosure of exemplary embodiments of a mold, illustrated by way of example in the accompanying drawings, wherein:

FIG. 3 shows a view of an enlarged scale detail of FIG. 2, FIG. 4 shows an exploded view of the mold of FIG. 1 with a molded piece;

FIGS. 5 to 8 show views similar to FIGS. 1 to 4, respectively, in accordance with a variant of the present invention.

In the accompanying drawings, identical parts or components are identified by the same numerals.

EXAMPLES OF EMBODIMENTS OF THE INVENTION

Figure 1:
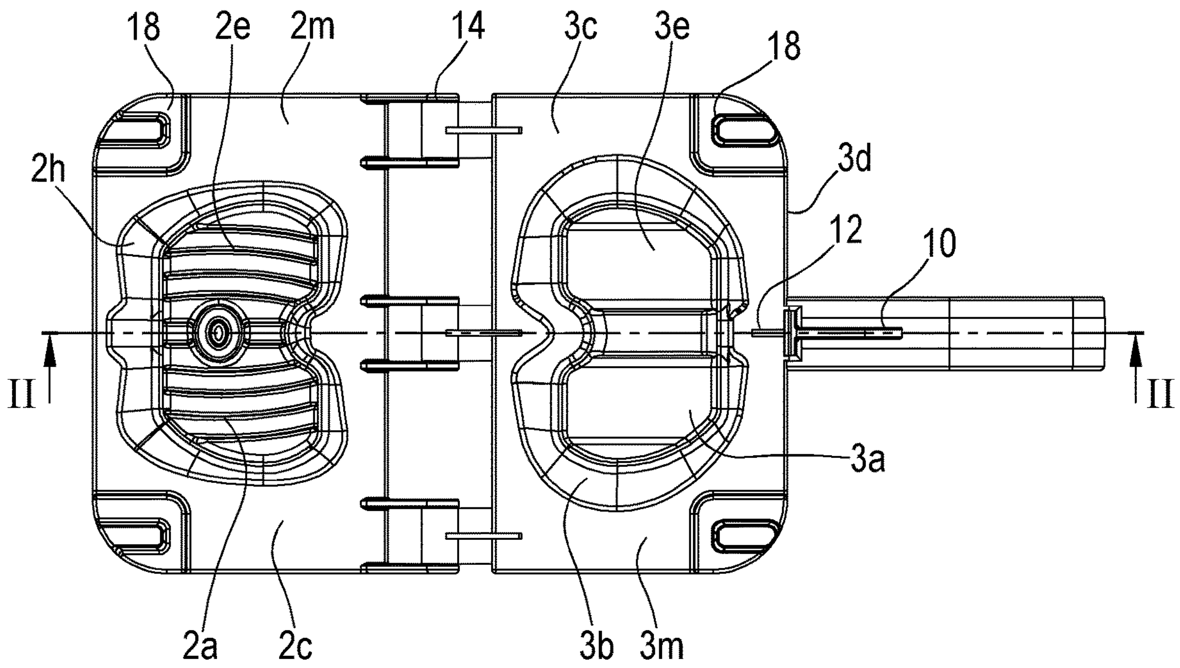
FIG. 1 shows a top view of a mold according to the present invention.
Figure 2:
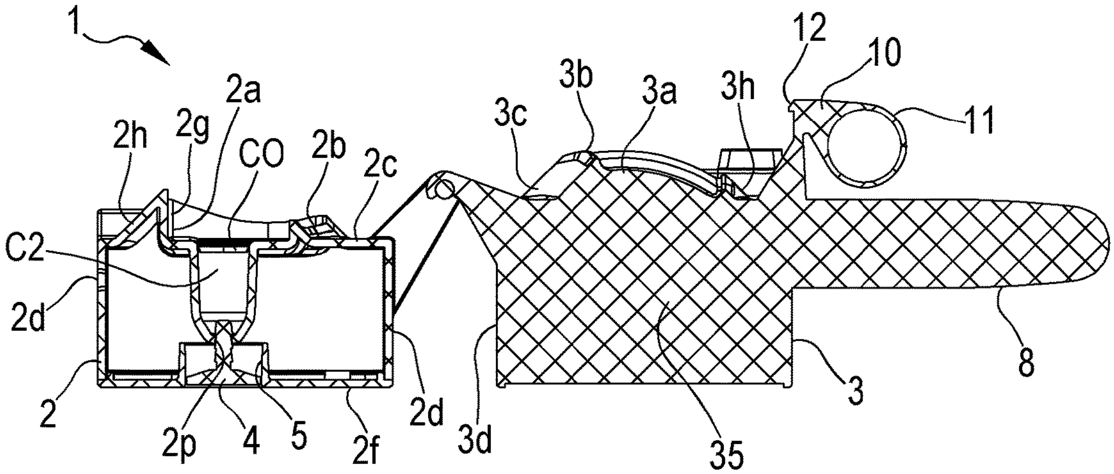
FIG. 2 shows a sectional view taken along the II-II plane line of FIG. 1.

With reference to FIGS. 1 to 4, a mold 1 for obtaining or forming a spacer device TS for the replacement of a joint prosthesis or a part thereof, for example a knee spacer device, such as a tibial component thereof, that is to say an element adapted to be implanted in use at the tibial bone of the knee joint, is illustrated.

Naturally, a mold according to the present invention can also be used for obtaining a spacer device of a different type, such as a hip or shoulder spacer device.

As is standard practice, spacer devices are temporary, disposable apparatuses implanted in the human body, for example at a joint in the human body, to replace a permanent joint prosthesis. This is basically because the implant of the permanent joint prosthesis is infected and it therefore becomes necessary, on the one hand, to treat the infection after removing the infected prosthesis and, on the other, to protect the joint space until a new prosthesis is implanted in the point from which the infection has been removed.

These functions are performed by the spacer devices, which are made of a suitable biocompatible material, such as a bone cement based on an acrylic resin, for example polymethyl methacrylate, possibly with the addition of at least one medical substance with an antimicrobial effect (for example, at least one antibiotic to treat the infection at the implant site). The most commonly used antibiotics are one of gentamicin or vancomycin or combinations thereof. This material, in at least one version of the invention, comprises bone cement, based, for example, on polymethyl methacrylate (PMMA).

The antibiotic or blend of antibiotics is mixed with bone cement by the doctor on the basis of, for example, the indications of the pharmacologist who will have evaluated the specific bacterial or pathogenic flora of the patient. The resulting material or mass is used to form the most effective spacer device for eradicating the infection in the specific patient.

The material that constitutes the mold, although rigid, is free of additives that can be extracted and/or absorbed by the bone material or cement that will constitute the spacer device during manufacture. The extraction and/or absorption of the additives present in the mold is a very serious problem that arises, for example, in molds made of elastomers, such as silicone, and so forth. As is evident, if the material of the molded spacer device has in its mass any additives extracted and/or absorbed by the material constituting the mold, this undermines the safety of the spacers molded with such molds from a toxicological point of view. Since early 2018, many molds of this type have been withdrawn from the global market.

A mold 1 according to the present invention comprises, in detail, a first half-shell 2 including or delimiting a first forming surface 2*a* delimited by a first perimeter or peripheral or ring-shaped edge 2*b* and intended to shape at least one first portion, or rather, at least one first face, of the spacer device TS.

The mold then comprises a second half-shell 3 including or delimiting a second forming surface 3*a* delimited by a second perimeter or peripheral or ring-shaped edge 3*b* and intended to shape at least one second portion or face of the spacer device TS.

The two half-shells 2, 3 are adapted to be coupled in use in a removable way so as to define a closed configuration for the mold and to delimit between them, at the first forming surface 2*a* and the second forming surface 3*a*, a molding cavity C1, for example a main molding cavity C1, corresponding to the external configuration of the spacer device TS, or of a part thereof, to be formed.

The two half-shells 2, 3 are then movable between an open configuration, for loading the material to be molded or for removing the molded spacer device, and a closed molding configuration.

The first forming surface 2*a* and/or the second forming surface 3*a* constitutes/constitute the area of application of the material that will constitute the spacer device to be formed with the mold 1 according to the present invention and are respectively intended to shape at least one first face and at least one second face of the spacer device TS.

With particular reference to FIGS. 1 to 4, the first forming surface 2*a* is adapted to form a first portion or face, e.g., lower TS1 of the tibial knee spacer device TS, while the second forming surface 3*a* is adapted to form a second portion or face, e.g., upper TS2 of the spacer device TS.

The upper face TS2 is adapted in use to be articulated with a femoral knee spacer device or with the femoral end of a knee joint of a patient, while the lower face TS1 is adapted in use to be implanted at the end of the patient's tibial bone at the knee joint.

If desired, the first forming surface 2*a* and/or the second forming surface 3*a* is also adapted to form a third portion or face, for example lateral TS3 (defining, in fact, the thickness) of a tibial knee spacer device TS.

Clearly, the first perimeter edge 2*b* is adapted to abut and come into contact, in use and more particularly in the closed configuration, with the second perimeter edge 3*b*.

Moreover, the mold 1 comprises at least one extractor component 4 intended to remove a spacer device TS, or a part thereof, formed in the mold 1 when the latter is in an open configuration, with the first half-shell 2 moved away from and not in contact (see FIG. 1 or 2), at least at the perimeter edges 2*b*, 3*b*, with the second half-shell 3. Basically, in the open configuration, the two forming surfaces 2*a*, 3*a* are not facing each other with the two perimeter edges 2*b*, 3*b* in contact and defining the molding cavities C1, C2.

The extractor component 4 is, of course, a mechanical structural component and not a chemical compound applied on the forming surfaces 2*a*, 3*a* or on the delimiting walls of a molding cavity C1, C2.

Preferably, the extractor component 4 is integrated and, if desired, constrained or removably or non-removably connected to a respective semi-mold 2, 3.

Advantageously, the extractor component 4 is movable between a rest position and at least one extraction position in the direction going from within a respective half-shell 2, 3 towards the respective forming surface 2*a*, 3*a*, so as to determine the detachment of a spacer device from the latter. In essence, the spacer device 4, 104 does not act beginning from the forming surface 2*a*, 3*a* and moving towards the inside of the respective half-mold 2, 3, but rather from the inside of the latter towards the respective forming surface 2*a*, 3*a*.

Even more advantageously, the extractor component 4 is housed in a seat 5 delimited by said first half-shell 2 or by said second half-shell 3 and is mounted in a movable way in said seat 5 between a rest position, in which it does not protrude within said at least one molding cavity C1, C2 (which will be discussed in more detail later) or relative to a respective forming surface 2*a*, 3*a*, or else protrudes therein by a first magnitude and at least one extraction position in which it protrudes at least partially within a molding cavity C1 or C2 or relative to a respective molding surface 2*a*, 3*a* by a greater magnitude than the rest position.

Preferably, the extractor component 4 has first engagement means 6, while a respective half-shell 2, 3 has at the seat 5 second engagement means 7 designed to engage with the first engagement means 6 at least when the extractor component 4 is moved from the rest position to at least an extraction position. In this regard, advantageously, the engagement between the first 6 and the second 7 engagement means prevents or limits the return of the extractor component 4 to the rest position.

If desired, the first engagement means 6 can comprise first teeth or projections or recesses, while the second engagement means 7 can comprise second recesses or openings or protuberances for engagement of the first engagement means.

Clearly, more engagement means 6, 7 may be provided, so as to ensure a greater number of points or areas of non-return of the extractor component.

It is also possible to provide third engagement means 60 in or of the extractor component 4 that can be engaged with engagement means of a respective half-shell 2, 3, such that the extractor component 4 is prevented from moving away from the molding cavity C1, C2 or the respective forming surface 2*a*, 3*a* in the rest position. With regard to this possibility, mounting the extractor component 4 in the seat 5 could determine the engagement between the third engagement means 60 and second engagement means of a half-shell 2, 3, which would prevent a displacement, as now indicated.

With reference to this aspect, the third engagement means 60 can comprise third teeth or projections or recesses which can also be engaged with the second engagement means 7, including second recesses or openings or protuberances for engagement of the third engagement means.

In the rest position, the extractor component 4 is preferably unable to determine the detachment of a spacer device TS from the surfaces of the mold 1.

Advantageously, the seat 5 is, on the one hand, open towards the forming surface 2*a*, 3*a* of the respective half-shell 2, 3 and, on the other, towards the outside of the mold 1, so that, from outside the mold 1, the extractor component 4 can be manually pressed or moved or controlled to take it from a rest position to an extraction position.

Optionally, the extractor component 4 has a base portion 4*a* and a stem portion 4*b* extending from the base portion and designed to engage a spacer device TS, or a part thereof, formed in the mold.

If first engagement means 6 are present, they can be formed in the stem portion 4*b*. The same applies to any third engagement means 60.

In this respect, one of the half-shells 2, 3 may delimit an opening or through hole 2*p* leading into a molding cavity C1 or C2 or into a respective forming surface 2*a*, 3*a*. In said opening or through-hole, the portion or stem 4*b* is also slidably inserted, with teeth 6 designed to define shoulders 6*a* facing away from said at least one cavity C1 or C2 and designed to abut against internal sections of the half-shell zone 2, 3 that delimit the opening or through-hole 2*p*. The same applies to any third engagement means 60.

Conversely, the engagement means may consist of one, two, three or more teeth, ring-shaped or otherwise, formed on the stem portion 4*b*. If several teeth are provided, they may be spaced along the extension of the stem portion 4*b*.

Advantageously, the stem portion 4*b* has, between its free end 4*b*1 and a first tooth 6 or shoulder 6*a*, ring-shaped or otherwise, an increasing cross-section and the same applies in any sections between adjacent and subsequent shoulders 6*a*.

If several teeth are provided, then the tooth or teeth 60 near or closest to the free end 4*b*1 act(s) as third engagement means, while the next tooth or teeth act(s) as first engagement means 6.

In this case, the sections of the half-shell 2, 3 defining the opening or through hole 2*p* are elastically yielding, so that, by inserting the stem portion 4*b*, the latter enlarges the opening or through hole 2*p* until a shoulder 6*a* reaches and overcomes the latter, when the tooth 6, or rather, the respective shoulder 6*a*, engages by snapping onto the internal sections 7 of the zone of the half-shell 2, 3 delimiting the opening or through hole 2*p*.

In such circumstances, it would be difficult, if not impossible, to move the extractor component 4 backwards, since the teeth 6 would substantially prevent such movement, unless special tools were used and by means of difficult manoeuvres.

Clearly, there could also be an inverse structure to the one here disclosed, with one or more openings in the stem portion 4*b* and with teeth or projections in one of the half-shells 2, 3, for example starting from a delimiting wall of an opening or through hole defined by one of the half-shells.

As will become clear below, and as already partly indicated, the extractor component 4 has the function of extracting the spacer device once the latter has been formed and the material of which it is composed has hardened.

Preferably, as indicated above, the extractor component 4 is of a substantially unidirectional type, so that it has a non-return geometry that makes the mold 1 disposable.

This aspect is very important because, after having produced a spacer device, the mold might undergo changes or alterations caused precisely by the polymerisation and/or hardening reaction of the material that constitutes the device itself and which could compromise the correct functioning of the mold during subsequent uses. Such a mold should therefore not be re-used more than once. In addition, in the event of use, it would be necessary to sterilise the two half-shells and the other components, and the sterilisation phase might also cause modifications or alterations that could compromise correct functioning.

Moreover, only the use of a disposable mold ensures optimal sterility of the spacer device obtained with it.

In at least one version of the invention, the two half-shells, or rather, the respective forming surfaces differ from each other and do not mirror each other.

With reference to the step of obtaining or forming a spacer device, the first half-shell 2 can also be a lower body in use, while the second half-shell 3 can also be an upper body in use, considering the support plane on which the mold 1 in closing configuration can rest during the step of forming the respective spacer device TS. The second half-shell 3 can therefore act as a cover for the first half-shell 2.

During the forming phase, the mold 1 is therefore in a closed operating configuration. Conversely, during the loading phase of the material that constitutes the spacer device the mold is advantageously in an open operating configuration. In the open configuration, the first 2 and the second 3 half-shells can both rest on a support plane and/or be placed side by side.

If desired, the mold 1, if provided for making a knee spacer device with a stem TS4, can delimit a special secondary molding cavity C2 (seen, for example, in FIG. 1 or 3) open towards the first forming surface 2*a*. The secondary cavity C2 is delimited only by a half-mold, e.g. the first half-mold 2, while the first molding cavity C1 is delimited between the first forming surface 2*a* and the second forming surface 3*a*.

In this case, therefore, the cavity C1 delimited between the first 2*a* and the second 3*a* forming surface substantially determines the formation of the tibial plate TS5 that has a substantially rectangular or oval or C shape in the plan view and a thickness given by the distance between the lower face TS1 and the upper face TS2 of the spacer device TS, while the secondary cavity C2 substantially determines the production of the stem TS4 of the spacer emerging from the tibial plate TS5.

However, the main cavity C1 and the secondary cavity C2 are contiguous to each other and/or in fluid connection, so that the material that goes to form the spacer device TS can flow (during the forming step) into both such cavities C1, C2 and form, in one step, both the tibial plate TS5 and the stem TS4 of the spacer device TS, which constitute one piece.

If desired, a handle 8, possibly removable, is present at one of the half-shells 2, 3 of the mold 1.

The surgeon or the personnel in charge of producing or forming the spacer device TS by means of the mold 1 may use this handle 8 to bring the first half-shell 2 into abutment against the second half-shell 3 (or vice-versa) and to apply adequate force to compress the material that will constitute the spacer device itself.

Indeed, the mold 1 is preferably not an injection mold and loading of the material into the mold 1 will be illustrated in greater detail in the continuation of the present disclosure.

The first half-shell 2 and/or the second half-shell 3 may have a substantially block-like or a solid or empty body conformation, for example substantially box-like or tub-shaped or polyhedral, possibly parallelepipedal or rectangular or cylindrical.

The walls (in the case of a box-like body) or faces (in the case of a solid block) of the half-shells 2, 3 can, for example, be substantially triangular, square or rectangular, possibly with bevelled edges. More particularly, two walls or faces are of larger dimensions and lie on two planes parallel to each other and parallel to the support plane on which the mold 1 is adapted to be placed, while the other at least three walls or faces (four in the attached Figures) constitute the lateral extension that perimetrically connects the two walls or faces of greater dimensions, for example in a substantially perpendicular manner to the latter.

Conversely, in the case of a cylindrical conformation of one or both half-shells, there are two substantially larger, circular or oval faces and a side wall or face, possibly tubular, extending from the perimeter or circumference of at least one of the larger walls or faces to the other.

With specific reference to the exemplary embodiment illustrated in the Figures, the first half-shell 2 comprises at least one first wall or main face, for example upper 2*c* in use, wherein the first forming surface 2*a* is defined or delimited and a lateral extension 2*d* consisting of one or more walls or side faces, preferably extending from an outer edge of the main face 2*c*.

In this case, the seat 5 is delimited in the area defined between the first wall or main face 2*c* and the lateral extension 2*d*.

Moreover, there may also be a second wall or main face, for example lower 2*f* in use. Alternatively, the first half-shell 2 may be open, for example lower in use. The second wall or main face 2*f* effectively closes the half-shell 2.

If provided, the second main wall 2*f* may be removably or non-removably constrained, for example by glue, snap-on engagement or other similar means to the other walls of the second half-shell 2, or to the walls of the lateral extension 2*d*, if desired. In this regard, tabs 2*fl* can be provided to engage respective grooves 2*q* in the walls of the lateral extension 2*d* or vice versa.

If desired, the first forming surface 2*a* is defined substantially centrally or in an intermediate position to the first main face 2*c*.

In this respect, the first forming surface 2*a* may comprise a first base 2*e*, in recess with respect to the upper wall or face 2*c* and/or the first peripheral edge 2*b*, and a first section of side wall or surface 2*g*. The first portion of the side wall or surface 2*g* extends from the perimeter of the first base 2*e* to the first peripheral edge 2*b*. The first section of the side wall or surface 2*g* is perpendicular or defines a tapered section approaching or receding from the first base 2*e*. The first perimeter edge 2*b* can then be raised or staggered with respect to the first base 2*e* and/or the first wall or upper main face 2*c*.

In general, at least one of the first perimeter edge 2*b* and the second perimeter edge 3*b* is raised respectively with respect to the wall or face of the first half-shell or lower body 2 or second half-shell 3.

Naturally, together with the first base 2*e*, the side section 2*g* also contributes to the shape of the spacer device TS resulting from forming in the mold 1. Thus, the first base 2*e* and the side section 2*g* will be conformed correspondingly, albeit negatively, to at least the lower face TS1 and to at least part of the thickness TS3 of the tibial plate TS5.

Furthermore, at the first base 2*e*, positioned substantially centrally, a fluid communication opening CO may be provided between the zone defined by the first forming surface 2*a* and the possible secondary cavity C2 for the stem TS4 of the spacer device TS in question.

The first base 2*e* may have a series of (first) ribs 2*n* adapted to determine the formation of respective (first) longitudinal grooves TS6 of the lower face TS1 of the tibial plate TS5.

A first raised or projecting wall portion 2*h*, for example annular, may then be provided between a first intermediate portion of the wall or upper face 2*c* and the first peripheral edge 2*b*. The section of raised wall 2*h* can be substantially inclined or perpendicular with respect to the peripheral area of the upper face 2*c* and, in at least one version of the invention, is tapered when approaching the first peripheral edge 2*b*.

Preferably, in at least one version of the invention, the remaining part 2*m* of the first wall or main face 2*c* surrounding the first forming surface 2*a*, as well as, if present, the first peripheral edge 2*b*, the first base 2*e* and the raised wall section 2*h*, is flat and substantially coplanar.

In substantially the same manner, the second half-shell, if desired in use, an upper body 3, comprises at least one respective first wall or main face, for example lower 3*c* in use, wherein the second forming surface 3*a* and a lateral extension 3*d* comprising one or more side walls or faces, preferably extending from an outer edge of the main face 3*c*, are defined or delimited, for example in a substantially central position. There can also be a second wall or main face, for example upper in use. Alternatively, the second half-shell 3 may be open at the top and thus be tub-shaped.

If desired, the second half-shell 3 is therefore an empty body with internal stiffening walls 3*s*.

The second forming surface 3*a* may comprise a second base 3*e*. In one version of the invention and/or in at least some areas thereof, the second base 3*e* is staggered relative to a lateral portion of the lower face or wall 3*c*.

The second half-shell 3 also comprises a second section of wall or side surface 3*g*. The second section of wall or lateral surface 3*g* extends along the perimeter of the second base 3*e*, from the latter to the second peripheral edge 3*b*. The second section of wall or side surface 3*g* is perpendicular or defines a tapered section approaching or receding from the second base 3*e*. The second perimeter edge 3*b* may then be raised or staggered relative to the second base 3*e* and/or generally to the first top wall or main face 3*c*.

Naturally, together with the second base 3*e*, the side surface 3*g* also contributes to the shape of the spacer device TS resulting from its forming in the mold 1. Therefore, the second base 3*e* and the side section 3*g* will be shaped correspondingly, albeit negatively, to at least the upper face TS2 and part of the thickness or part of the third portion or side face TS3 of the tibial plate TS.

In particular, the second base 3*e* can have a substantially smooth surface, although, in at least one version of the invention, comprising a central longitudinal recess 3*n* to obtain a rectangular base protrusion TS7 present at the upper face TS2 of the tibial plate TS4.

A second raised or projecting wall section 3*h* may then be provided between a first intermediate portion of the wall or upper face 3*c* and the second peripheral edge 3*b*. The section of raised wall 3*h* can be substantially inclined or perpendicular with respect to the peripheral area of the wall or lower face 3*c* and, in at least one version of the invention, it is tapered on approaching the second peripheral edge 3*b*.

Preferably, in at least one version of the invention, the remaining part 3*m* of the first wall or main face 3*a* surrounding the second forming surface 3*a*, as well as, if present, the second peripheral edge 3*b*, the second base 3*e* and the raised wall section 3*h*, is flat and substantially coplanar.

The handle 8, if present, can be removably or non-removably constrained at the front or rear area in use of one of the half-shells, for example of the second half-shell 3.

Furthermore, at the lateral extension 2*d* or 3*d* of at least one of the two half-shells, removable constraining means 10 may be provided for the removable constraint of the two half-shells 2, 3.

With reference to the non-limiting exemplary embodiment illustrated in the Figures, the removable constraining means 10 comprise coupling means, for example snap-on, and possibly a trigger element 11.

More particularly, the removable coupling means 10 may comprise, for example, a tooth or protrusion element 12, integral or in one piece with one of the half-shells 2, 3, or rather, with a trigger element 11, itself integral or in one piece with one of the half-shells 2, 3, capable of engaging in a removable way in a suitable engagement seat 13 delimited in the other half-shell 3, 2 when the mold is in the closed position.

Naturally, it is also possible for the coupling means, if provided, to be placed in a different position than that indicated above or to be of a different structure.

In this regard, when the operator in charge of forming the spacer device closes the mold 1, bringing the first half-shell 2 and the second half-shell 3 into abutment against each other so as to form the cavity C1 between the first forming surface 2*a* and the first perimeter edge 2*b* and the second forming surface 3*a* and the second perimeter edge 3*a*, he/she can do so using the handle 8. By applying a force, for example a manual force, on the handle 8, he/she can couple the tooth or protrusion element 12, for example inside the engagement seat 13.

Once the forming phase has been completed, and therefore after having waited a predetermined time for the hardening of the material that constitutes the spacer device, the operator acts on the trigger element 11 to determine the release and/or uncoupling of the tooth or protrusion element 12 from the engagement seat 13. If the trigger element 11 is in the vicinity of the handle 8, the operator can, in substantially one-step, grip the handle 8, release the coupling means 10 using the trigger 11 and move the second half-shell 3 away from the first half-shell 2 and, by angularly moving or roto-translating one half-shell 2 in relation to the other 3, if desired by means of the handle 8, cause the mold 1 to open.

Advantageously, the two half-shells 2, 3 are hinged or can be hinged to each other. In this regard, there are hinged or reciprocal displacement means with constraint 14, for example at the rear area in use of the first half-shell 2 and/or the second half-shell 3. These hinged or reciprocal displacement means with constraint 14 allow the rotation or angular displacement (around a special fulcrum or centre of rotation, if desired) or reciprocal roto-translation of the second half-shell 3 with respect to the first half-shell 2, bringing them into abutment with each other and thus causing the mold 1 to close.

Conversely, such hinged or reciprocal displacement means with constraint 14 also make possible the rotation or roto-translation of the release between the first 2 and second 3 half-shells, resulting in the opening of the mold 1. In this phase, the first forming surface 2*a* and the second forming surface 3*a* obviously move away from each other while in the mold closing phase they approach each other, until the cavity C1 and, possibly, the secondary cavity C2 are determined.

As a result of the presence of the hinged or reciprocal displacement means with constraint 14, it is possible to ensure perfect coupling between the first peripheral or perimeter edge 2*b* of the first half-shell 2 and the second peripheral edge 3*b* of the second half-shell 3.

In this respect, the first perimeter edge 2*b* and the second perimeter edge 3*b* abut against each other when the mold is closed, guaranteeing a substantially sealed closure and maintaining a complete contact and/or a complete adherence with each other along their entire extension. Thus, the first perimeter edge 2*b* is in abutment against and/or matches and/or corresponds to the second perimeter edge 3*b*. In this way, the spacer device resulting from the forming phase does not require further finishing or cutting phases of the molding burr. The peripheral edges 2*b* and/or 3*b* can also act like a knife that cuts the molding burr directly during the forming phase.

In one version of the invention, the two edges have flat abutment surfaces that come into direct contact with each other. These abutment surfaces may be substantially parallel to the support plane of the mold 1 or both have the same inclination, outward or inward, with respect to the cavity C1.

In an alternative version, there are no hinged or reciprocal displacement means with constraint 14, and first half-shell 2 and second half-shell 3 are moved away from and/or brought closer to each other according to other methods known in the field.

Regarding the detail of the extractor component 4 referred to in the exemplary embodiment in the Figures, it can include a base portion 4*a*, discoidal or of another shape, if desired, and a stem portion 4*b*, of lower section to the base portion 4*a* and emerging from the latter, said stem portion 4*b* having a free tip or end 4*c*. The base portion 4*a* is opposite the free tip or end 4*c*.

If desired, in the resting position the free tip or end 4*c* protrudes in use in the main cavity C1 or, if provided, secondary cavity C2, and therefore occupies a small part of the space intended for forming the stem TS4. Accordingly, and if desired, a small cavity or recess, created precisely by such tip or end 4*c* protruding into the cavity C1 or C2 in the rest position, may be provided in the distal end of the stem TS4 of the spacer device TS at the end of the molding method.

Clearly, the tip or end 4*c* may not protrude into the secondary cavity C2 in the rest condition of the extractor component 4, so that there would be no cavities or recesses in the spacer device TS determined by the tip 4*c* of the extractor component 4.

The stem 4*b* may then have a substantially rod or pin-like conformation extending from the base portion 4*a* and ending with the free tip or end 4*c*.

Advantageously, the half-shell 2, 3 in which the extractor component 4 is at least partially housed has, at the respective first 2*a* or second 3*a* forming surface, a through hole 2*p* provided at the bottom of the secondary cavity C2 or the cavity C1 and intended to allow the extractor component 4, or rather the respective tip 4*c*, to pass or to advance towards the respective surface 2*a*, 3*a* when the base portion 4*a* is pressed to extract the spacer device 4.

Preferably, the extractor component 4 is in one piece.

If desired, the base portion 4*b* is mounted at an opening or housing area 5*a* (which constitutes a part of the seat 5) in the second main face or wall, for example lower 2*f* in use of the first half-shell 2, possibly flush with the latter, at least in the rest position of the extractor component 4. In this respect, a sleeve section 2*s* emerging from the second face or main wall 2*f* may be provided, which sleeve 2*s* may delimit a through channel for insertion and housing of the base portion 4*a* of the extractor component 4.

Conversely, the free tip or end 4*c* is positioned at the main cavity C1 or secondary cavity C2, in particular at the area of said secondary cavity C2 distal from the respective forming surface 2*a*. In a version in which the secondary cavity C2 is not present, the tip or end 4*c* may or may not protrude into the cavity C1 at least in the extraction position, but, if desired, can protrude slightly when the extractor component 4 is in the rest position.

As already partly indicated, the first half-shell 2 can delimit a housing area 5*a* for the base portion 4*a*, at an intermediate or central ring-shaped section 2*s* of the second main wall 2*f*, if desired, the cross-section of which corresponds to the cross-sectional conformation (e.g., circular) of the base portion 4*a* and the height of which preferably corresponds at least to the stroke of the extractor component 4 in the transition from the rest position to an extracting position.

In use, according to the non-limiting exemplary embodiment illustrated in the Figures, the operator in charge of forming the spacer device, once the latter is formed, after the mold 1 is opened, will press or act, for example manually, on the base portion 4*a*, so that the tip or end 4*c* presses against the stem TS4 or against the lower face TS1 of the tibial plate TS and determines the exit of the formed spacer device TS from the mold 1 and/or its movement away from the forming surface 2*a* of the first half-shell 2.

Clearly, in the transition from the rest position to the extraction position the extractor component 4 and, more particularly, the respective free tip or end 4*c*, is inserted completely into the main cavity C1 or, if present, secondary cavity C2, so as to push the spacer device TS out of said cavity or cavities C1, C2 or through the forming surface 2*a*, 3*a* and then extract or detach the spacer device TS from the mold 1 in which it has been formed or from a respective half-shell 2, 3.

If desired, the engagement means 6 of the extractor component 4 comprise a series of protrusions or lateral teeth shaped, for example, like a dovetail and extending externally with respect to the stem 4*b*.

The extractor component 4 can be made, in whole or in part, of a deformable material, which allows the passage of the tip or end 4*c* through the special hole 2*p* present at the bottom of the secondary cavity C2 or of the main cavity C1 when the base portion 4*a* is pressed to extract the spacer device 4, but do not allow it to escape or return to its backward resting position.

In this way, part of the stem 4*b* remains within the secondary cavity C2 or main cavity C1, effectively preventing a second or subsequent use of the mold 1.

If desired, the second forming surface 3*a* of the second half-shell 3 has no undercuts. Thus, once molded, the spacer device will remain constrained (albeit temporarily) only to the first forming surface 2*a* of the first half-shell 2 and to the cavity C1. In this way, it is easier to remove the spacer device formed by the first half-shell 2, for example using the extractor component 4.

Alternatively, if the second forming surface 3*a* also has undercuts and/or cavities, special extraction means (not illustrated) could also be provided from the second undercut, or application of detaching means could be contemplated, at least on the second forming surface 3*a* (or possibly also on the first forming surface 2*a*), such as to facilitate the detachment of the spacer device after its formation.

Of course, the extractor component 4 could be provided also or only in the second half-shell 3.

Abutment blocks 18 may be present at the sides of the mold 1 and at the first wall or main face 2*c*, the first half-shell 2 and/or the second half-shell 3. Such blocks 18 are placed, for example, at the corners of the walls and/or faces of the half-shells 2, 3, for example at the top, bottom or sides thereof.

These blocks 18 may have complementary shapes or surfaces between blocks present at the first half-shell 2 and blocks present in the second half-shell 3 or between blocks present at the first half-shell 2 or relative housings present at the second half-shell 3 or vice-versa, so as to facilitate closure of the mold 1 and maintenance of the correct forming space when the second half-shell 3 is closed onto the first half-shell 2, or vice-versa.

Such blocks 18 may protrude or be recessed in a wall or face of the half-shells.

If desired, when the mold is closed the blocks 18 can determine the realisation of a space between the first face or wall 2*c* of the first half-shell 2 and the face or wall, possibly the upper face or wall 3*c* of the second half-shell 3, or better, between the respective parts 2*m* and 3*m*, in which the material that will constitute the spacer device can possibly flow if present in excess with respect to the quantity necessary to obtain the device itself. As a result of the presence of the first peripheral edge 2*b* and the second peripheral edge 3*b*, any excess and leaking material will be eliminated (cut) when the same edges are brought into contact with each other and the two half-shells 2, 3 are brought into abutment and tightened together, for example by means of the removable constraining structure 10.

The height of the blocks 18 facilitates perfect contact between the first peripheral edge 2*b* and the second perimeter edge 3*b* when the mold 1 is in the closed configuration.

In the mold 1, the first perimeter edge 2*b* and the second perimeter edge 3*b* constitute, respectively, the access openings for the first half-shell 2 and the second half-shell 3. The material making up the spacer device TS can be introduced through such access openings, or at least through the access opening determined by the first perimeter edge 2*b* of the first half-shell 2.

As a result of the mold according to the present invention, the material making up the spacer device TS can have a very high viscosity. In fact, the forces involved in the mold 1 closing step, as well as the specific conformation thereof, also facilitate compression of a very dense and/or viscous material, ensuring that the same flows over the entire area consisting of the cavity C1 and the secondary cavity C2, without leaving empty spaces, and obtaining a fully formed spacer device TS.

Moreover, as a result of the conformation of the mold 1, active pressure is created which compresses and deforms the material constituting the spacer device, causing it to flow into all the areas of the cavity C1 and/or the secondary cavity C2, so as to obtain a perfect filling of the latter by the material in question, with consequent optimal forming of the spacer device in all its parts.

The material constituting the spacer device is supplied to the mold by casting and/or placement on the first forming surface 2*a* and/or the second forming surface 3*a*, but, as mentioned, not by injection into the mold 1.

In particular, in at least one version of the invention, the above material is positioned at the first forming surface 2*a*. In an alternative version, the material may be positioned at the second forming surface 3*a* or on both the first forming surface 2*a* and the second forming surface 3*a*.

Figure 5:
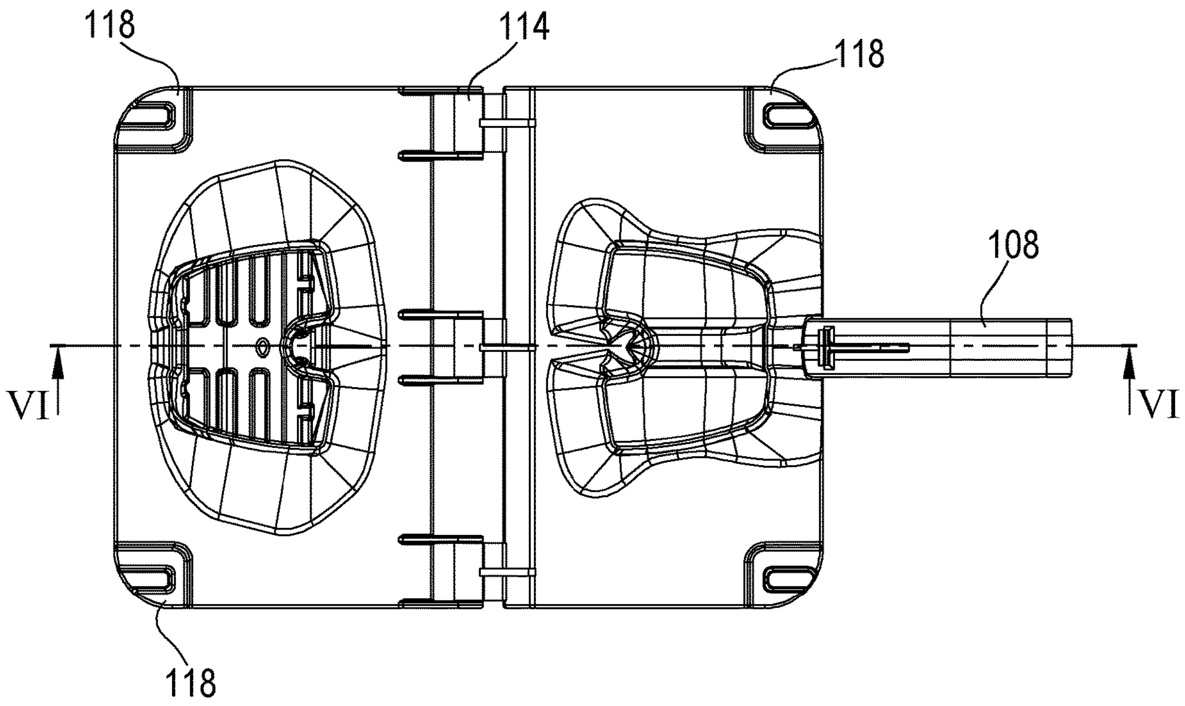
Figure 6:
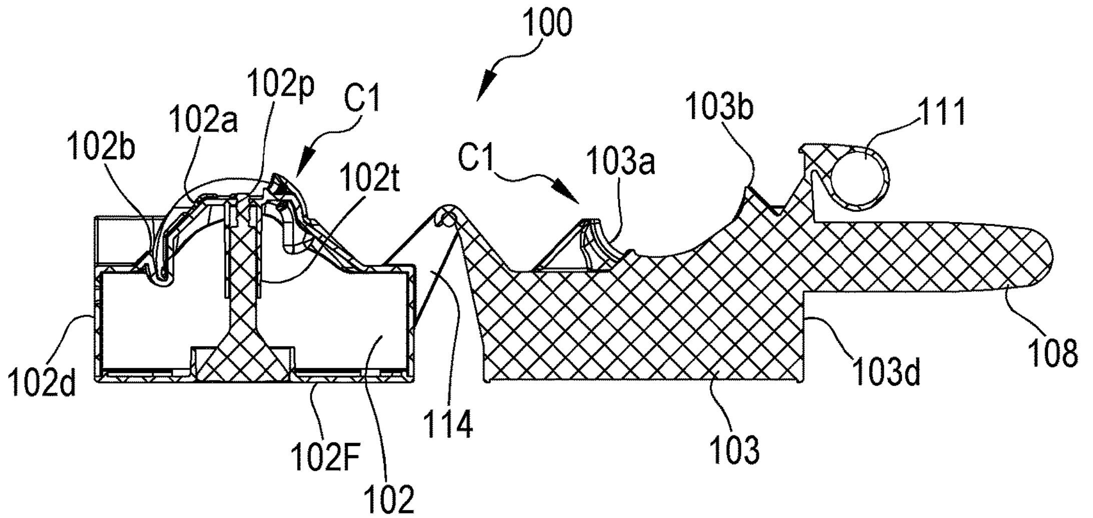

With regard to FIGS. 5 to 8, reference will now be made to a mold 100 for forming the femoral knee spacer device FS.

Elements identical to the previous embodiment will be indicated with the same reference number increased by one hundred units.

Unless otherwise expressly indicated, the features and elements described for the previous exemplary embodiment may be present and provide the same results also for the mold 100, to which reference will now be made.

The mold 100 is very similar to the mold 1 for obtaining the tibial knee spacer device. What changes most are the forming surfaces, which in the mold 100 are dedicated to obtaining the femoral knee spacer device FS.

The mold 100 thus comprises a first half-shell, lower 102 in use, if desired, comprising a first forming surface 102*a*, and a second half-shell, upper 103 in use, if desired, comprising a second forming surface 103*a*, and a cavity C1 defined between the first half-shell 102 and a second half-shell 103 (or rather, by their forming surfaces 102*a* and 103*a*), when the latter are coupled together and in the closed position.

The first forming surface 102*a* is delimited by a first perimeter edge 102*b*, while the second forming surface 103*a* is delimited by a second perimeter edge 103*b*. The first peripheral edge 102*a* is adapted to be brought into abutment against the second peripheral edge 103*b*, as disclosed for the first embodiment.

With particular reference to the Figures indicated, the first forming surface 102*a* is adapted to form the upper face FS2 of the femoral knee spacer device FS, while the second forming surface 103*a* is adapted to form the lower face FS1 of the spacer device FS.

The lower face FS1 is adapted to be articulated with the tibial knee spacer device (for example, the one illustrated in FIG. 4, or a generic tibial knee spacer device), or with the tibial end of a knee joint of a patient, while the upper face FS2 is adapted in use to be implanted at the end of the femoral bone of the patient at the knee joint.

Advantageously, both the first forming surface 102*a* and the second forming surface 103*a* have a curved profile. In particular, the first forming surface 102*a* has a convex pattern, while the second 103*a* has a concave pattern.

The cavity C1 substantially determines the formation of the femoral component of the knee spacer device that has a substantially rectangular or oval or C-shaped conformation in the plan view, and a thickness given by the distance between the upper face FS2 and the lower face FS1 of the spacer device FS.

A handle 108, possibly removable, is present at the second half-shell 103, completely similar to the handle 8 disclosed for the first embodiment.

The first half-shell 102 and the second half-shell 103 substantially have a solid or empty block conformation or a box-like or tub-shaped conformation.

The first half-shell 102 therefore comprises at least one wall or main face, for example upper 102*c* in use, in which the first forming surface 102*a* and a lateral extension 102*d* consisting of one or more wall or side faces are defined or delimited, while a second wall or face, for example lower 102*f*, may or may not be present.

The first forming surface 102*a* consists of a first base 102*e* that is convex with respect to the upper face 102*c*, and a first section of wall or side surface 102*g*. The first side wall or surface portion 102*g* extends from the perimeter of the first base 102*e* to the first perimeter edge 102*b*. The first perimeter edge 102*b* is therefore raised with respect to the base 102*e* and/or the upper face 102*c*. The first perimeter edge 102*b* can then be raised or staggered with respect to the first base 102*e* and/or the first wall or upper main face 102*c*.

In particular, the base 102*e* may have a series of ribs 102*n* adapted to determine the formation of respective longitudinal grooves FS5 of the upper face FS2 of the body of the femoral spacer FS.

A first raised or projecting wall portion 102*h* may then be provided between a first intermediate portion of the wall or top face 102*c* and the first peripheral edge 102*b*. The raised wall section 102*h* can be substantially inclined or perpendicular to the peripheral area of the upper face 102*c* and, in at least one version of the invention, is tapered in proximity to the first peripheral edge 102*b*.

In a substantially similar manner, the second half-shell or upper body 103 can comprise at least one first wall or main face, for example lower 103*c* in use, in which the second forming surface 103*a* and a lateral extension 103*d* consisting of one or more walls or side faces is defined or delimited, for example in a substantially central position.

The second forming surface 103*a* consists of a base 103*e* which is concave with respect to the upper wall or face 103*c*. In one version, the second base 103*e* rises from the lower wall 103*c* and the second perimeter edge 103*b* is therefore raised with respect to the lower face 103*c*.

In particular, the second base 103*e* may have a substantially smooth surface, although, in at least one version of the invention, it comprises a longitudinal central rib 103*p* corresponding to a rectangular base recess FS6 present at the lower face FS1 of the femoral spacer device FS.

The first main face 103*c* is connected to the second peripheral edge 103*b* by a raised surface 103*h*, substantially inclined or inclined or perpendicular to the peripheral area of the upper face 103*c* and, in at least one version of the invention, is tapered on approaching the first peripheral edge 103*b*.

With regard to the handle 108, if present it can be provided and constrained at the front or rear area in use of one of the half-shells, for example the second half-shell 3.

Furthermore, at the lateral extension 102*d* or 103*d* of at least one of the two half-shells, removable constraining means 111 may be provided for the removable constraint of the two half-shells 102, 103, for example as disclosed with reference to the embodiment of FIGS. 1 to 4.

Advantageously, the two half-shells 102, 103 are hinged or can be hinged to each other. In this regard, hinged or displacement means with constraint 114, for example, are present at the rear area in use of the first half-shell 102 and/or the second half-shell 103.

In addition, in at least one version of the invention the mold 100 can also comprise an extractor component 104.

The extractor component 104 may include a base portion 104*a* and a stem portion 104*b* with a free end or tip 104*c*. The base portion 104*a* is opposite the free tip or end 104*c*.

The base portion 104*a* is mounted at an opening in the second main face or wall, for example lower in use of the second main face 102*c* of the first half-shell 102, possibly flush with the latter. Conversely, the free tip or end 104*c* is positioned at the cavity C1, in particular at a central area thereof, for example. The tip or end 104*c* presses against the upper surface FS2 of the femoral spacer device FS through a special hole 102*p* present at the cavity C1 and/or at the first forming surface 102*a*, and causes the ejection of the spacer device formed by the mold 100 and/or the cavity C1 of the first half-shell 102.

In this case, the base portion 104*b* is mounted at an opening or housing area 105*a* in the second face or main wall, for example lower 102*f* in use of the first half-shell 102, possibly flush with the latter, at least in the rest position of the extractor component 104. In this respect, a sleeve section 102*s* emerging from the second face or main wall 102*f* may be provided, which sleeve 102*s* may delimit a through channel for insertion and housing of the base portion 104*a* of the extractor component 104.

A tubular guide portion 102*t* that extends from the first wall or main face 102*c* in the direction of the second wall or face 102*f* can also be provided to guide the stem portion 104*b*, the tubular guide section 102*t* of which flows into the hole 102*p*.

If desired, the engagement means 106 of the extractor component 104 comprise a series of lateral protrusions extending externally with respect to the stem 104*b*, shaped, for example, like a dovetail, the disclosure of which has been made for the exemplary embodiment of FIGS. 1 to 4 and referred to herein.

Again, the mold 100 may comprise abutment blocks 118 similar to those of the example of FIGS. 1 to 4.

Figure 9:
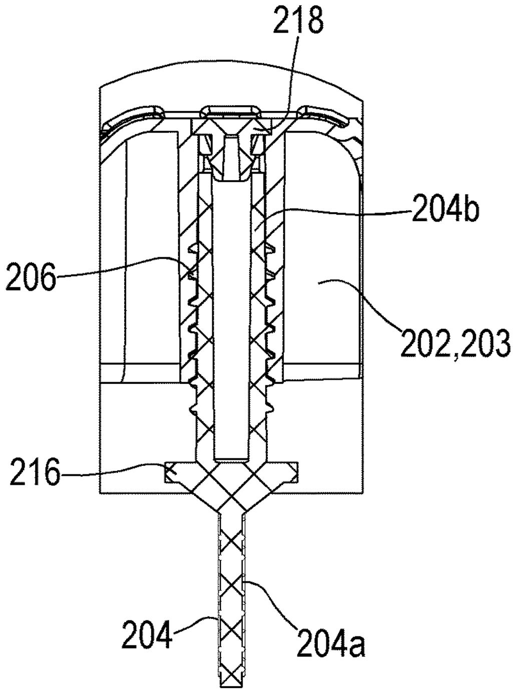
FIG. 9 shows a view of a detail of the engagement zone between the extractor and the respective seat in a half-shell of another mold according to the present invention.
Figure 10:
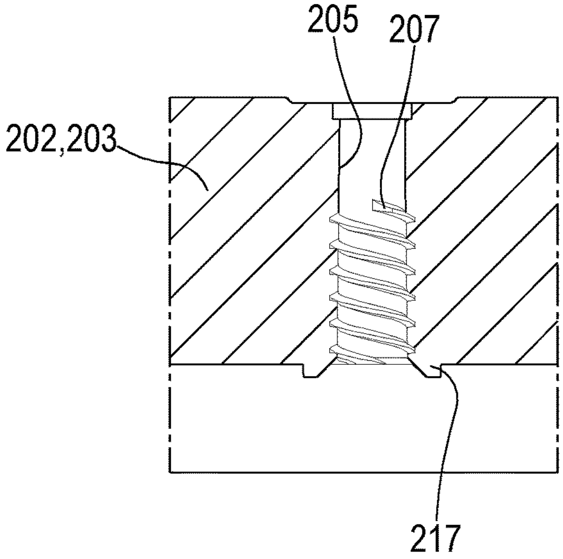
FIG. 10 shows a view of a detail of the positioning or engagement zone of the mold partially shown in FIG. 9, FIGS. 11 and 12 show perspective views of an extractor component for the mold partially shown in FIG. 9.
Figure 11:
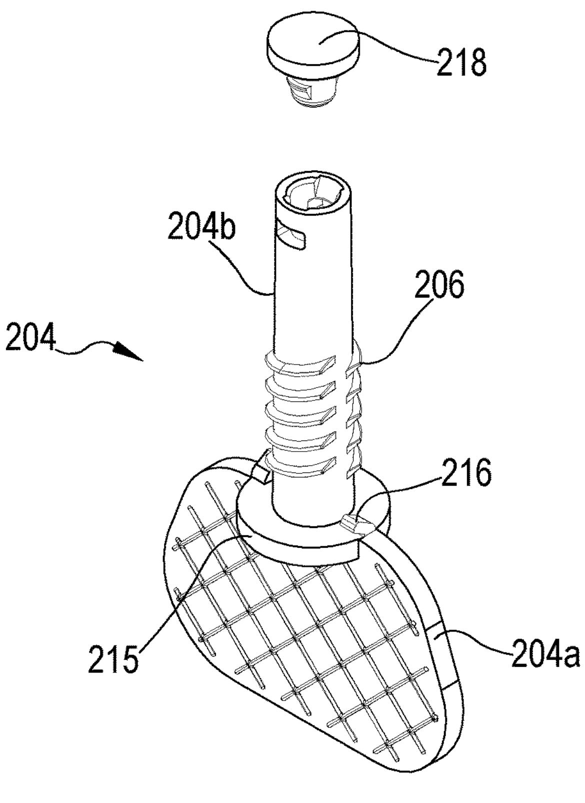
Figure 12:
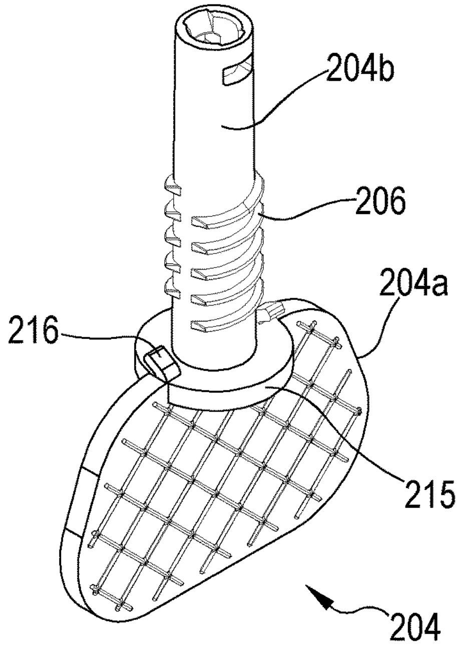

Referring now to FIGS. 9 to 12, these illustrate a mold variant in accordance with the present invention, the extractor component 204 of which includes, as first engagement means, a thread or thread sections 206, while a respective half-shell 2, 3 has, at the respective seat 205, second engagement means 207 that define an internal thread section in the seat 205 designed to engage by being screwed to the first engagement means 206 when the extractor component 204 is moved from the rest position to at least one extraction position.

If desired, the extractor component 204 has a base portion 204*a* and a stem portion 204*b*, which is, if desired, tubular, with a section that is, for example, polygonal (regular or not) or circular, emerging from the base portion 204 and prepared, directly or not, to engage a spacer device TS, or a part thereof, formed in the mold.

In such cases, the thread or thread portions 206 are formed on, or extend externally from, the stem portion 204*b*.

According to this variant, the extractor component 204 can also be provided with means adapted to prevent, or in any event signal, the possible unscrewing or uncoupling from the respective half-shell 202, 203.

More particularly, if desired the extractor component 204 can have a support portion 215, e.g., a plate or disc portion from which the stem portion 204*b* extends and is interposed between the base portion 204*a* and the latter.

One, two or more teeth or wings 216 can extend from the plate or discoidal portion 215, if desired with a base end or constraint to the support portion 215, as well as a free end, which teeth or wings are substantially bent or curved so as not to extend parallel to the axis of the stem portion 204*b*, and so as to bring the respective free end close to, or cause it to be bent closer to, a section of the support portion 215 angularly staggered with respect to the constraint or connection of the respective base end.

If multiple wings 216 are provided, for example two, three or more, they may be equally angularly staggered (or not) and are preferably all bent in the same direction, e.g., all with the free end staggered angularly in a clockwise direction (considering the rotation about the axis of the stem portion 204*b*) in relation to the respective base end or vice versa.

Clearly, the teeth or wings 216 extend from the face of the base portion 215 facing the tip of the stem portion 204*b*.

On the other hand, the half-shell 202, 203 has at, or rather, on, the defining edge of the mouth or the end for the insertion of the extractor component 203 into the respective seat 205, one or more projections 217, for example two or more, angularly staggered between each other, if desired.

As a result of this precaution, once the extractor component 204 is engaged or inserted into the seat 205, the wing or wings 216 will, during screwing or rotation (counterclockwise according to the non-limiting exemplary embodiment in the Figures), repeatedly engage with the projection or projections 217 and, as the wings 216 are bent, the rotation necessary for screwing the first 206 and second 207 engagement means for the advancement of the extractor component 204 into the seat 205 will not cause the wings 216 to break, since the projections 217 will engage the wing or wings on the side of their "convexity", hence on their side facing the tip of the stem portion 204*b*.

In the event that, at the end of the molding and after extraction of the molded piece, a rotation is commanded in the opposite direction (clockwise according to the non-limiting exemplary embodiment in the Figures) of the extractor component 204, so as to unscrew the first 206 and second 207 engagement means, this would result in the breaking of the wing(s) 216 by the one or more projections 217 which would engage the wing(s) on the side of their "concavity" and then on the side facing away from the tip of the stem portion 204*b*.

Such measures would in fact ensure that the mold is used only once and that it is therefore disposable, thus meeting the above-mentioned requirements in this respect, since on attempting to remove the extractor component 204 for subsequent use, the broken fin(s) 216 would show that the mold has already been used and cannot (or rather must not) be reused.

Clearly, other arrangements may also be put in place to reveal a possible extraction of the extractor component 204 for an attempt at reuse.

According to the non-limiting exemplary embodiment illustrated in the Figures, the extractor component 204 also comprises a plug component 218 mounted onto the tip of the stem portion 204*b*. This can, be achieved, for example, by making the stem portion 204*b* hollow, at least at the respective tip, and by inserting into the latter a shank, or the like, of the plug component 218, then obtaining an engagement between these elements 204*b*, 218 which can, if desired, be removable, in any suitable manner, for example a snap-on, bayonet, interlocking or similar engagement.

In this respect, the plug component 218 would be the one that would actually grasp the molding cavity C1 and engage the TS spacer, or a part thereof, to determine its removal once molded.

In such cases, the plug component 218 could be made of the same material as the respective half-shell 202, 203, while the other elements of the extractor component 204, such as the base portion 204*a* and the stem portion 204*b*, could be made (in one piece with each other) of a different, for example more resistant, material.

Thus, for example, if the mold is made of polypropylene or other primary material, the base portion 204*a* and the stem portion 204*b* could be made of glass fibre-filled nylon or another suitable secondary material which is more rigid than polypropylene or the primary material and which, however, cannot or should not be brought into contact with the spacer TS material.

As will be appreciated, with a mold according to the present invention it is possible to implement a method for extracting a spacer device, or a part thereof, from a mold 1, 100.

According to this method, after a spacer device TS or FS, or a part thereof, has been molded, the mold is opened by moving away the first half-shell 2, 102, 202 and the second half-shell 3, 103, 203, so that the spacer device TS or FS, or a part thereof, remains in contact with one of the half-shells 2, 3, 102, 103, 202, 203, or better, with a single forming surface 2*a*, 3*a*, 102*a*, 103*a*.

At this point, the extractor component 4, 104, 204 is activated so as to move the spacer device TS or FS away from the half-mold 2, 3, 102, 103, 202, 203 with which it is in contact, or better, from a respective forming surface 2*a*, 3*a*, 102*a*, 103*a*.

Advantageously, when the extractor component 4, 104, 204 is activated it is moved between a rest position and an extraction position, in which the extractor component 4, 104, 204 protrudes within a molding cavity C1, C2 or through a forming surface 2*a*, 3*a*, 102*a*, 103*a* to a greater extent than the rest position.

Preferably, the extractor component 4, 104, 204 is operated manually by pressing against or acting on a base portion 4*a*, 104*a*, 204*a* thereof, starting from a wall or zone of the respective half-shell 2, 3, 102, 103, 202, 203 which is opposite that of delimitation of the forming surface 2*a*, 3*a*, 102*a*, 103*a*, if desired.

Moreover, if engagement means 6, 7, 106, 107 are provided, then, once the extractor component 4, 104, 204 is actuated, the first engagement means 6, 106, 206 engage the second engagement means 7, 107, 207. In such cases, the engagement between the first 6, 106 and second 7, 107 engagement means may prevent or limit the return to the rest position of the extractor component 4, 104.

As will be appreciated, a mold according to the present invention allows easy and quick extraction of a spacer device formed therein.

Moreover, if engagement means are provided they ensure that the mold is used only once and that it is therefore disposable, thus meeting the needs indicated above in relation to this feature.

Modifications and variants of the invention are possible within the scope of protection defined by the claims.

The invention claimed is:

1. A mold for obtaining a spacer device (TS, FS) for replacing a joint prosthesis or a part thereof, comprising:

- a first half-shell (2, 102, 202) comprising or delimiting a first forming surface (2*a*) delimited by a first perimeter edge (2*b*) and designed to shape at least one first portion of said spacer device (TS, FS); and
- a second half-shell (3, 103, 203) comprising a second forming surface (3*a*) delimited by a second perimeter edge (3*b*) designed to shape at least one second portion of said spacer device (TS, FS),
- wherein said first half-shell (2, 102, 202) and said second half-shell (3, 103, 203) are configured to be removably coupled, in use, so as to define a closed configuration for said mold and to delimit between said first forming surface (2*a*) and at said second forming surface (3*a*) at least one molding cavity (C1, C2) corresponding to an external configuration of the spacer device (TS, FS) or of the part thereof to be formed, and
- wherein said mold comprises,
  - a seat extending from an outer surface of said mold to said at least one molding cavity, and
  - at least one extractor component (4, 104, 204) housed at least partly in said seat and arranged to remove the spacer device (TS, FS) or the part thereof formed in the mold by causing a pressure to be exerted on the spacer device when the mold is in an open configuration, with said first half-shell (2, 102, 202) removed from, and not in contact with, said second half-shell (3, 103, 203).

2. The mold according to claim 1, wherein said at least one extractor component (4, 104, 204) is displaceable between a rest position and at least one extraction position in a direction from an inside of a respective half-shell (2, 3) towards a respective forming surface (2*a*, 3*a*), so as to determine a detachment of the spacer device from the respective forming surface.

3. The mold according to claim 1, wherein said at least one extractor component (4, 104, 204) is mounted so as to be movable in said seat (5, 205) between a rest position, in which said at least one extractor component does not protrude within said at least one molding cavity (C1, C2) or relative to a respective forming surface (2*a*, 3*a*) or protrudes therein for a first amount, and at least one extraction position, in which said at least one extractor component protrudes at least partially within said at least one molding cavity (C1, C2) or relative to a respective forming surface (2*a*, 3*a*) by an amount greater than the rest position.

4. The mold according to claim 3, wherein said at least one extractor component (4) has first engagement means (6, 106, 206), and wherein a respective half-shell (2, 3, 102, 103) has at said seat (5, 205) second engagement means (7, 107, 207) designed to engage said first engagement means (6, 106, 206) at least when said at least one extractor component (4, 104, 204) is moved from the rest position to the at least one extraction position.

5. The mold according to claim 4, wherein the mold is configured to cause an engagement between said first (6, 106) and said second (7, 107) engagement means to prevent or limit a return to the rest position of said at least one extractor component (4, 104).

6. The mold according to claim 4, wherein said first engagement means (6, 106) comprise first teeth or projections or recesses, and wherein said second engagement means (7, 107) comprise second recesses or openings or protuberances for engaging said first engagement means.

7. The mold according to claim 4, wherein said seat (5, 205) is open on the respective forming surface (2*a*, 3*a*) of the respective half-shell (2, 3, 102, 103), and on an outside of the mold on the outer surface of said first half-shell or of said second half-shell that is opposite to said first forming surface or respectively said second forming surface, so that starting from an outside of the mold said at least one extractor component (4, 104, 204) can be manually pressed or moved to take said at least one extractor component from a rest position to an extraction position.

8. The mold according to claim 7, wherein said at least one extractor component (4, 104, 204) has a base portion (4*a*, 104*a*) and a stem portion (4*b*, 104*b*) protruding from said base portion (4*a*, 104*a*) and is designed to engage the spacer device (TS, FS) or the part thereof formed in the mold.

9. The mold according to claim 8, wherein at least one of said first half-shell or said second half-shells (2, 3) defines an opening or through hole (2*p*, 102) opening into said at least one molding cavity (C1 or C2) or into a respective forming surface (2*a*, 3*a*, 102*a*, 103*a*), and wherein said portion (4*b*, 104*b*, 204*b*) is slidably inserted into said through opening or hole (2*p*, 102*p*).

10. The mold according to claim 9, wherein said stem portion (4*b*, 104*b*) has teeth (6, 106) designed to define shoulders (6*a*) facing away from said at least one molding cavity (C1 or C2) and designed to abut against internal sections of a half-shell zone (2, 3, 102, 103) delimiting said through opening or hole (2*p*).

11. The mold according to claim 10, wherein said stem portion (4*b*) has a free end (4*b*1) from which a first tooth (6)

or shoulder (6*a*) extends having an increasing cross-section, and an additional tooth (6) or shoulder (6*a*) of increasing cross-section extending in sections between adjacent and subsequent shoulders (6*a*).

12. The mold according to claim 7, wherein at least one of the first or the second half-shell (2, 102) comprises at least one first wall or main face (2*c*, 102*c*) where the respective forming surface (2*a*, 102*a*) and a lateral extension (2*d*, 102*d*) consisting of one or more side wall or faces extending from the first wall or main face (2*c*, 102*c*) are defined or delimited, said seat (5, 250) being delimited in a zone defined between said at least one first wall or main face (2*c*, 102*c*) and said lateral extension (2*d*, 102*d*).

13. The mold according to claim 12, further comprising at least one second wall or main face (2*f*, 102*f*) for closing said half-shell (2, 102, 202).

14. The mold according to claim 12, wherein at least one of the first or the second half-shell (2, 3) delimits a secondary cavity (C2) open towards the first forming surface (2*a*, 102*a*), and wherein said at least one extractor component (4, 104, 204) protrudes into said secondary cavity (C2) at least in said extraction position.

15. The mold according to claim 13, wherein said base portion (4*b*, 104*b*) is mounted at an opening or housing area (5*a*, 105*a*) in a second face or main wall (2*f*, 102*f*) of the first or the second half-shell (2, 102), and wherein a sleeve section (2*s*, 102*s*) is provided which protrudes from a second face or main wall (2*f*, 102*f*), the sleeve section (2*s*, 102*s*) delimiting a through channel for an insertion and housing of the base portion (4*a*, 104*a*) of the at least one extractor component (4, 104).

16. The mold according to claim 4, wherein said first engagement means comprise a thread or thread sections (206), and wherein said second engagement means (207) define an internal thread section in the seat (205) designed to engage by being screwed to the first engagement means (206).

17. A method of extracting a spacer device or a part thereof from a mold according to claim 4, comprising:

after the spacer device (TS, FS) or the part thereof has been with said mold, opening said mold by moving apart said first half-shell (2, 102, 202) and said second half-shell (3, 103, 203), so that said spacer device (TS, FS) or said part thereof remains in contact with the first or the second half-shell (2, 3, 102, 103, 202, 203); and actuating said at least one extractor component (4, 104, 204) so as to remove said spacer device (TS, FS) or said part thereof from the first or the second half-shell (2, 3, 102, 103, 202, 203) or from the respective forming surface (2*a*, 3*a*, 102*a*, 103*a*) in contact therewith.

18. The method according to claim 17, further comprising, when said at least one extractor component (4, 104, 204) is actuated, moving said at least one extractor component between a rest position and an extraction position, in which said at least one extractor component (4, 104, 204) protrudes within said at least one molding cavity (C1, C2) or relative to a respective molding surface (2*a*, 3*a*) to a greater extent than in said rest position.

19. The method according to claim 17, wherein said at least extractor component (4, 104, 204) is actuated manually by pressing against or acting on a base portion (4*a*, 104*a*, 204) thereof.

20. The method according to claim 17, wherein after actuating said at least one extractor component (4, 104, 204), said first engagement means (6, 106, 206) engage said second engagement means (7, 107, 207), so that an engagement between said first (6, 106, 206) and said second (7, 107, 207) engagement means prevents or limits a return to the rest position of said at least one extractor component (4, 104, 204).

* * * * *